(12) United States Patent
Kim

(10) Patent No.: US 10,012,724 B2
(45) Date of Patent: Jul. 3, 2018

(54) ULTRASONIC DIAGNOSTIC APPARATUS AND METHOD OF CONTROLLING THE SAME

(71) Applicant: SAMSUNG MEDISON CO., LTD., Hongcheon-gun, Gangwon-Do (KR)

(72) Inventor: Deok Gon Kim, Seoul (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 413 days.

(21) Appl. No.: 14/799,315

(22) Filed: Jul. 14, 2015

(65) Prior Publication Data

US 2016/0131749 A1 May 12, 2016

(30) Foreign Application Priority Data

Nov. 6, 2014 (KR) ........................ 10-2014-0153533

(51) Int. Cl.
*G01R 27/28* (2006.01)
*G01R 27/00* (2006.01)
(Continued)

(52) U.S. Cl.
CPC ........ *G01S 7/52074* (2013.01); *A61B 8/5207* (2013.01); *G01S 7/52038* (2013.01);
(Continued)

(58) Field of Classification Search
CPC ..... A61B 8/5207; A61B 8/463; A61B 8/5246; A61B 8/467; G01S 7/52074;
(Continued)

(56) References Cited

U.S. PATENT DOCUMENTS 6,193,662 B1   2/2001   Hwang
6,283,919 B1 * 9/2001   Roundhill ................ A61B 8/08
                                                            600/458
(Continued)

FOREIGN PATENT DOCUMENTS

EP           3017767 A1 *  5/2016  ........... A61B 8/5207
JP         2004-208918 A    7/2004
(Continued)

OTHER PUBLICATIONS

Extended European Search Report dated Apr. 8, 2016 issued in European Patent Application No. 15175282.1.

*Primary Examiner* — Daniel Pihulic
(74) *Attorney, Agent, or Firm* — McDermott Will & Emery LLP

(57) ABSTRACT

Provided are an ultrasonic diagnostic apparatus that is capable of generating an image caused by fundamental components of ultrasonic echo signals and synthesizing the generated image with an image caused by harmonic components so that an image having both advantages of the images can be generated, and a method of controlling the ultrasonic diagnostic apparatus. The ultrasonic diagnostic apparatus includes: a transmission beam generating unit that generates a plurality of sets of transmission beams by setting transmission beams which are transmitted in different transmission scan line positions and in which the sum of waveforms is 0, to one set; a reception beam generating unit that generates reception beams with respect to at least one reception scan line in consideration of transmission delay of the transmission beams in each of the transmission scan lines; a signal processing unit that extracts fundamental components and harmonic components from the reception beams, respectively; a synthesization unit that generates synthesized signals by synthesizing the fundamental components and the harmonic components according to a set (Continued)

synthesization ratio; and a display unit that displays a synthesized image including the synthesized signals.

22 Claims, 19 Drawing Sheets

(51) Int. Cl.
 *G01S 7/52* (2006.01)
 *A61B 8/08* (2006.01)
 *G01S 15/89* (2006.01)
 *A61B 8/00* (2006.01)

(52) U.S. Cl.
 CPC ...... *G01S 7/52085* (2013.01); *G01S 7/52093* (2013.01); *G01S 7/52095* (2013.01); *G01S 15/8904* (2013.01); *G01S 15/8915* (2013.01); *G01S 15/8963* (2013.01); *A61B 8/463* (2013.01); *A61B 8/467* (2013.01); *A61B 8/5246* (2013.01)

(58) Field of Classification Search
 CPC ............ G01S 15/8904; G01S 7/52038; G01S 7/52093; G01S 15/8963; G01S 7/52085; G01S 7/52095; G01S 15/8915
 See application file for complete search history.

(56) References Cited

U.S. PATENT DOCUMENTS

| | | | |
|---|---|---|---|
| 6,436,046 B1 | 8/2002 | Napolitano et al. | |
| 6,589,177 B1 | 7/2003 | Detmer et al. | |
| 2002/0091318 A1 | 7/2002 | Chiao et al. | |
| 2002/0128555 A1 | 9/2002 | Maxwell et al. | |
| 2003/0176792 A1 | 9/2003 | Kawagishi et al. | |
| 2006/0241451 A1* | 10/2006 | Nakaya | A61B 8/0833 600/443 |
| 2007/0149879 A1* | 6/2007 | Roundhill | A61B 8/08 600/447 |
| 2008/0275345 A1 | 11/2008 | Bruce et al. | |
| 2010/0036255 A1 | 2/2010 | Itani | |
| 2016/0131749 A1* | 5/2016 | Kim | A61B 8/5207 367/7 |

FOREIGN PATENT DOCUMENTS

| | | | | |
|---|---|---|---|---|
| JP | 2006-340886 A | 12/2006 | | |
| JP | 2010-051375 A | 3/2010 | | |
| KR | 20160054227 A | * | 5/2016 | ........... A61B 8/5207 |
| WO | 99/30617 A1 | 6/1999 | | |

* cited by examiner

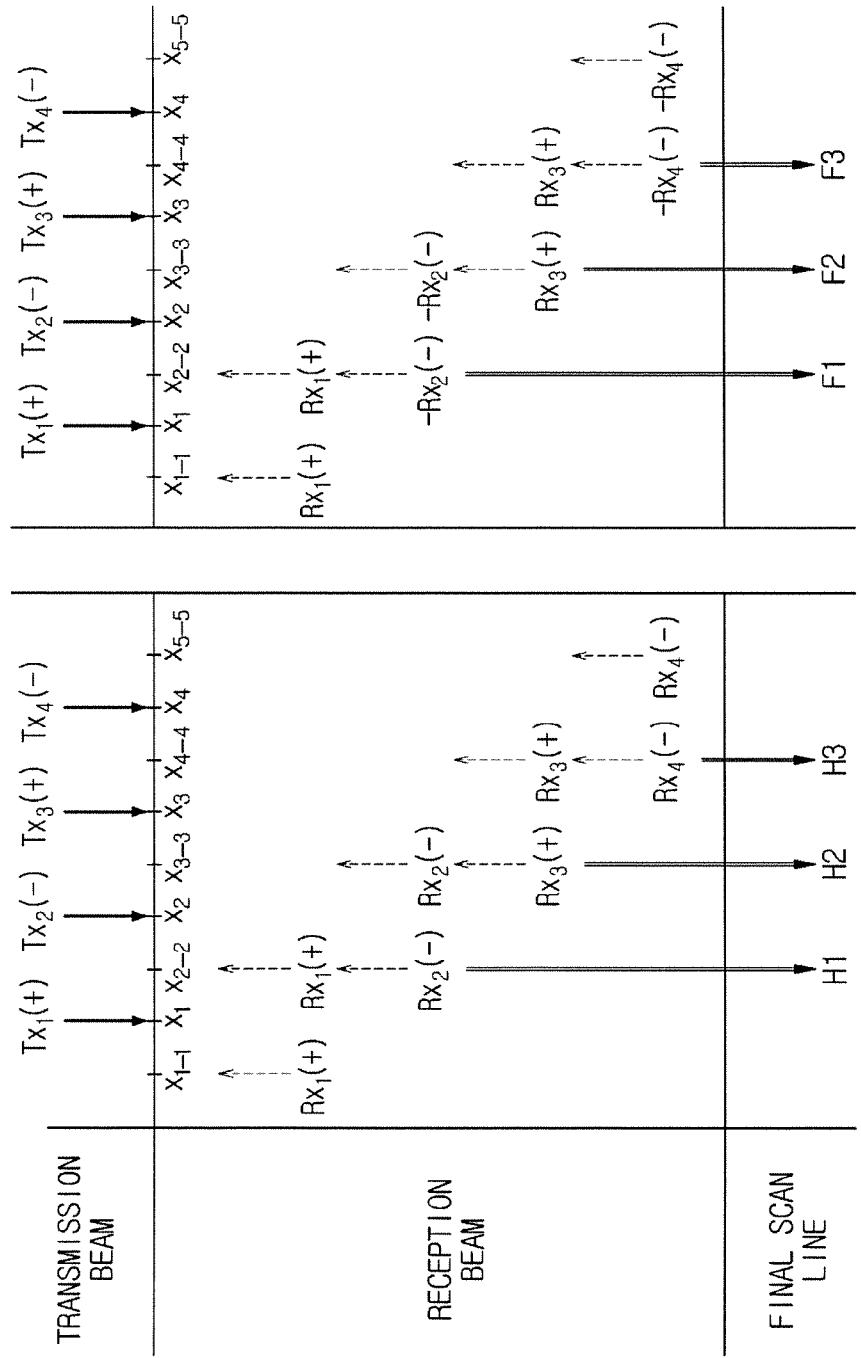

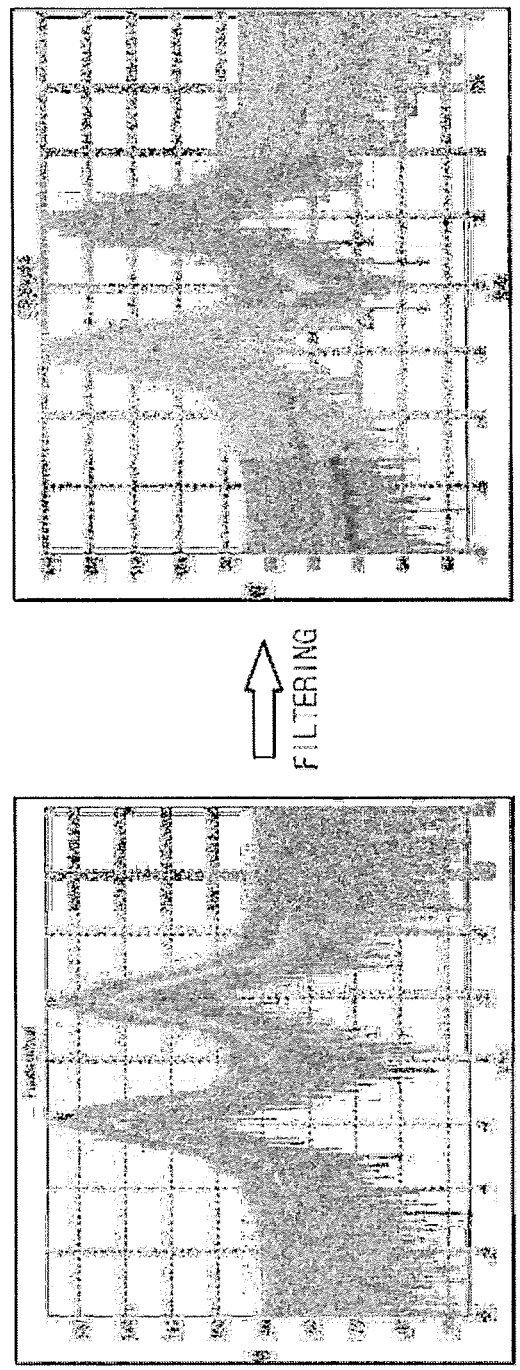

ULTRASONIC DIAGNOSTIC APPARATUS AND METHOD OF CONTROLLING THE SAME

CROSS-REFERENCE TO RELATED APPLICATION

This application claims the benefit of Korean Patent Application No. P10-2014-0153533, filed on Nov. 6, 2014 in the Korean Intellectual Property Office, the disclosure of which is incorporated herein by reference.

BACKGROUND

1. Field

Embodiments of the present invention relate to an ultrasonic diagnostic apparatus that is capable of imaging an inside of an object by using ultrasonic echo signals reflected from the object and returned, and a method of controlling the ultrasonic diagnostic apparatus.

2. Description of the Related Art

Since ultrasonic diagnostic apparatuses have non-invasive and non-destructive characteristics, the ultrasonic diagnostic instruments are widely used in the field of medicine so as to image an inside of an object or obtain information regarding a material that constitutes the inside of the object.

To this end, the ultrasonic diagnostic instruments transmit ultrasonic signals and receive ultrasonic echo signals reflected from the object and returned. The ultrasonic signals may be deformed by a reaction with a tissue that constitutes the inside of the object and thus, distortion occurs in waveforms of the ultrasonic signals. Thus, frequency sound waves that correspond to an integer multiple of fundamental frequency components may be included in the ultrasonic echo signals, and these frequency components are referred to as harmonic components.

SUMMARY

Therefore, it is an aspect of the present invention to provide an ultrasonic diagnostic apparatus that is capable of generating an image caused by fundamental components of ultrasonic echo signals and synthesizing the generated image with an image caused by harmonic components so that an image having both advantages of the images can be generated, and a method of controlling the ultrasonic diagnostic apparatus.

Additional aspects of the invention will be set forth in part in the description which follows and in part, will be obvious from the description, or may be learned by practice of the invention.

In accordance with one aspect of the present invention, an ultrasonic diagnostic apparatus includes: a transmission beam generating unit that generates a plurality of sets of transmission beams by setting transmission beams which are transmitted in different transmission scan line positions and in which the sum of waveforms is 0, to one set; a reception beam generating unit that generates reception beams with respect to at least one reception scan line in consideration of transmission delay of the transmission beams in each of the transmission scan lines; a signal processing unit that extracts fundamental components and harmonic components from the reception beams, respectively; a synthesization unit that generates synthesized signals by synthesizing the fundamental components and the harmonic components according to a set synthesization ratio; and a display unit that displays a synthesized image including the synthesized signals.

The ultrasonic diagnostic apparatus may further include an input unit to which selection of the synthesization ratio is input from a user.

The signal processing unit may extract the harmonic components by coupling the reception beams with respect to the same reception scan line.

The signal processing unit may extract the fundamental components by subtracting at least two reception beams among the reception beams with respect to the same reception scan line.

The signal processing unit may perform filtering on the extracted fundamental components and harmonic components.

The ultrasonic diagnostic apparatus may further include an image processing unit that generates a fundamental image including the fundamental components, a harmonic image including the harmonic components, and a synthesized image including the synthesized signals.

The display unit may further display the fundamental image and the harmonic image.

The display unit may display a synthesized image according to a synthesization ratio that changes when the synthesization ratio changes, in real time.

The ultrasonic diagnostic apparatus may further include a storing unit that stores the reception beams or the fundamental components and the harmonic components extracted from the reception beams.

In accordance with another aspect of the present invention, an ultrasonic diagnostic apparatus includes: a transmission beam generating unit that generates a plurality of sets of transmission beams by setting transmission beams which are transmitted in different transmission scan line positions and in which the sum of waveforms is 0, to one set; a reception beam generating unit that generates reception beams with respect to at least one reception scan line in consideration of transmission delay of the transmission beams in each of the transmission scan lines; a signal processing unit that extracts fundamental components and harmonic components from the reception beams, respectively; an image processing unit that generates a fundamental image including the fundamental components and a harmonic image including the harmonic components; a synthesization unit that generates a synthesized image by synthesizing the fundamental image and the harmonic image according to a set synthesization ratio; and a display unit that displays the synthesized image.

The ultrasonic diagnostic apparatus may further include an input unit to which selection of the synthesization ratio is input from a user.

The display unit may further display the fundamental image and the harmonic image.

In accordance with still another aspect of the present invention, a method of controlling an ultrasonic diagnostic apparatus, includes: radiating a plurality of sets of transmission beams onto different transmission scan line positions by setting transmission beams in which the sum of waveforms is 0, to one set; generating reception beams with respect to at least one reception scan line in consideration of transmission delay of the transmission beams in each of the transmission scan lines; extracting fundamental components and harmonic components from the reception beams, respectively; generating synthesized signals by synthesizing the fundamental components and the harmonic components according to a set synthesization ratio; and displaying a synthesized image including the synthesized signals.

The method may further include receiving selection of the synthesization ratio from a user.

The extracting of the fundamental components and the harmonic components from the reception beams, respectively, may include extracting the harmonic components by coupling the reception beams with respect to the same reception scan line.

The extracting of the fundamental components and the harmonic components from the reception beams, respectively, may include extracting the fundamental components by subtracting at least two reception beams among the reception beams with respect to the same reception scan line.

The extracting of the fundamental components and the harmonic components from the reception beams, respectively, may further include performing filtering on the extracted fundamental components and harmonic components.

The method may further include generating a fundamental image including the fundamental components and a harmonic image including the harmonic components.

The method may further include displaying the fundamental image and the harmonic image.

The displaying of the synthesized image may include displaying a synthesized image according to a synthesization ratio that changes when the synthesization ratio changes, in real time.

In accordance with yet still another aspect of the present invention, a method of controlling an ultrasonic diagnostic apparatus, includes: generating a plurality of sets of transmission beams in different transmission scan line positions by setting transmission beams in which the sum of waveforms is 0, to one set; generating reception beams with respect to at least one reception scan line in consideration of transmission delay of the transmission beams in each of the transmission scan lines; extracting fundamental components and harmonic components from the reception beams, respectively; generating a fundamental image including the fundamental components and a harmonic image including the harmonic components; generating a synthesized image by synthesizing the fundamental image and the harmonic image according to a set synthesization ratio; and displaying the synthesized image.

The method may further include receiving selection of the synthesization ratio from a user.

The method may further include displaying the fundamental image and the harmonic image.

The method may further include storing the reception beams or the fundamental components and the harmonic components extracted from the reception beams.

BRIEF DESCRIPTION OF THE DRAWINGS

These and/or other aspects of the invention will become apparent and more readily appreciated from the following description of the embodiments, taken in conjunction with the accompanying drawings of which:

FIGS. 7A and 7B are views for describing extraction of harmonic components and fundamental components;

FIGS. 8A and 8B through 10A and 10B are views of signal modeling of reception beams;

FIGS. 13A and 13B are graphs showing the result of filtering on the fundamental components;

DETAILED DESCRIPTION

Figure 1:
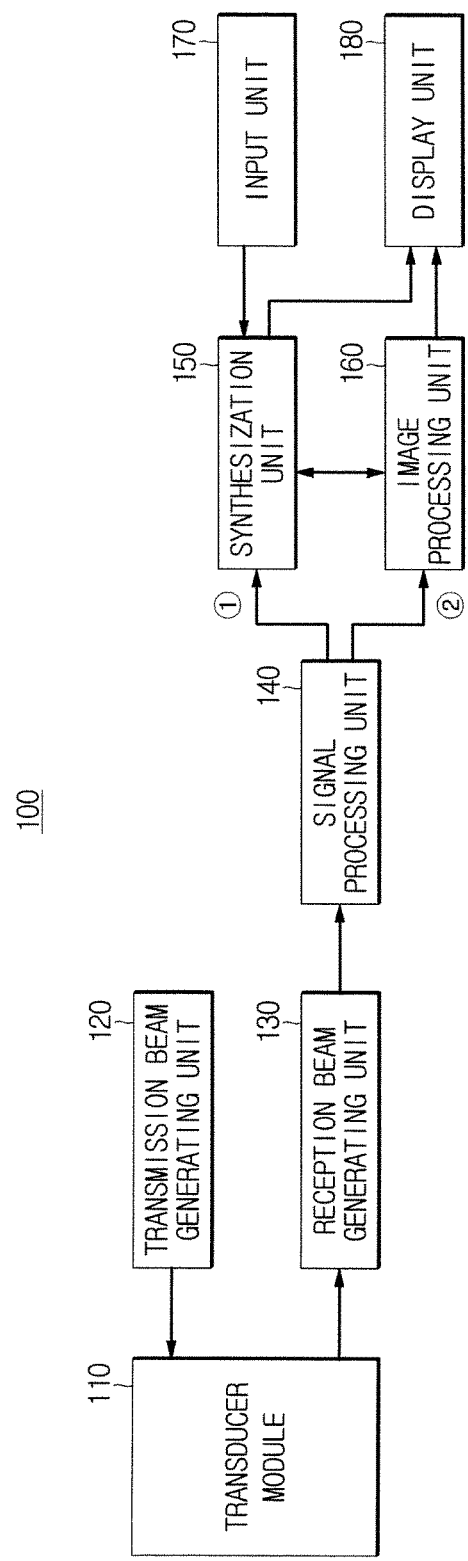
FIG. 1 is a control block diagram of an ultrasonic diagnostic apparatus in accordance with an embodiment of the present invention.

Reference will now be made in detail to the embodiments of the present invention, examples of which are illustrated in the accompanying drawings, wherein like reference numerals refer to like elements throughout.

Hereinafter, an ultrasonic diagnostic apparatus and a method of controlling the same in accordance with embodiments of the present invention will be described in more detail with reference to the accompanying drawings.

Figure 2:
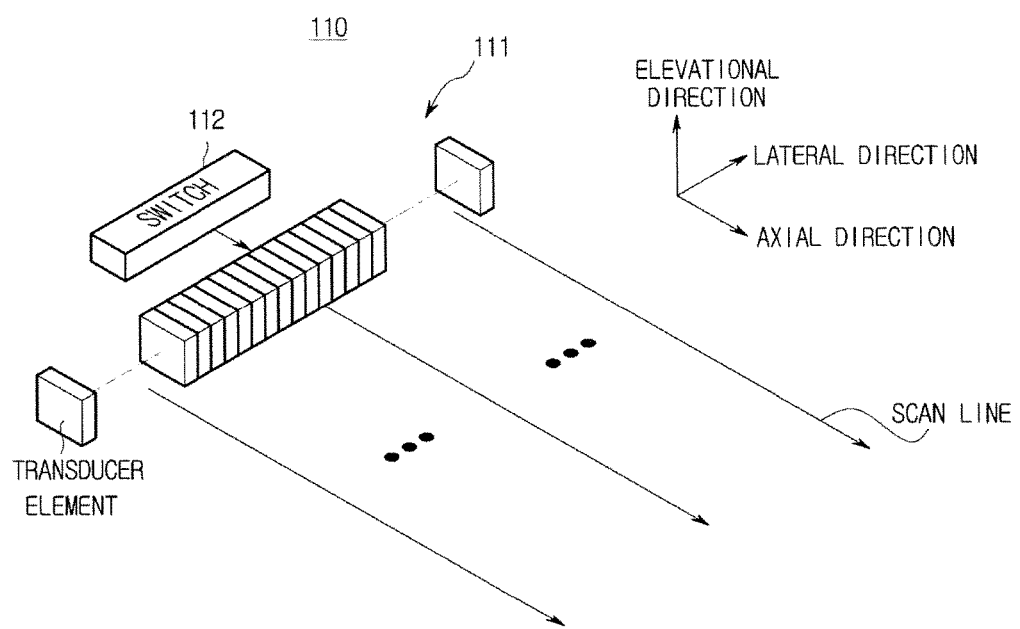
FIG. 2 is a view of a transducer array included in the ultrasonic diagnostic apparatus in accordance with an embodiment of the present invention.

FIG. 1 is a control block diagram of an ultrasonic diagnostic apparatus in accordance with an embodiment of the present invention, and FIG. 2 is a view of a transducer array included in the ultrasonic diagnostic apparatus in accordance with an embodiment of the present invention.

Referring to FIG. 1, an ultrasonic diagnostic apparatus 100 in accordance with an embodiment of the present invention includes a transducer module 110 that interconverts electrical signals and ultrasonic signals, a transmission beam generating unit 120 that generates transmission beams, a reception beam generating unit 130 that receives ultrasonic echo signals from the transducer module 110 and generates reception beams in a predetermined position, a signal processing unit 140 that extracts fundamental components and harmonic components by coupling reception beams in the same scan line position, a synthesization unit 150 that synthesizes two components or images generated by the two components according to a synthesization ratio of the extracted harmonic components with respect to the fundamental components, an image processing unit 160 that generates an ultrasonic image by performing image processing, such as compression or filtering, on frequency components extracted from the reception beams or synthesized signals obtained by synthesizing the frequency components, an input unit 170 to which selection of the synthesization ratio of the harmonic components with respect to the fundamental components is input, and a display unit 180 that displays the ultrasonic image on which image processing is performed.

The transducer module 110 may include a transducer array 111 including a plurality of transducer elements and a switch 112 that selects the plurality of transducer elements to be used to transmit and receive the ultrasonic signals, as illustrated in FIG. 2. In the current embodiment, the ultrasonic diagnostic apparatus 100 includes a one-dimensional transducer array 111. However, the embodiment of the ultrasonic diagnostic apparatus 100 is not limited thereto, and the ultrasonic diagnostic apparatus 100 may include a multidimensional transducer array 111.

Each of the transducer elements may interconvert the ultrasonic signals and the electrical signals. To this end, the transducer elements may be implemented with a magnetostrictive ultrasonic transducer using a magnetostrictive effect of a magnetic substance, a piezoelectric ultrasonic transducer using a piezoelectric effect of a piezoelectric material, or a piezoelectric micromachined ultrasonic transducer (pMUT) or may be implemented with a capacitive micromachined ultrasonic transducer (cMUT) that transmits/receives ultrasonic waves by using vibration of several hundreds or several thousands of micromachined thin films.

The transducer array 111 may be arranged in a linear form, as illustrated in FIG. 2, and may also be arranged in a convex form. In both cases, a fundamental operation principle of the transducer array 111 is the same. However, in a curved probe, ultrasonic beams transmitted from the transducer module 110 have a fan shape and thus, an ultrasonic image to be generated may be fan-shaped.

The switch 112 may be implemented with a multiplexer (MUX). However, embodiments of the present invention are not limited thereto, and any type of switch that may select a part of the plurality of transducer elements may be used as the switch 112.

A three-dimensional (3D) space in which ultrasonic imaging is performed, may be defined as a y-axis that corresponds to an elevational direction, an x-axis that corresponds to a lateral direction, and a z-axis that corresponds to an axial direction.

Spatial resolution of a two-dimensional ultrasonic image may be determined by axial resolution and lateral resolution. The axial resolution may refer to a capacity that may distinguish two objects arranged along an axis of ultrasonic beams, and the lateral resolution may refer to a capacity that may distinguish two objects arranged at a right angle to the axis of the ultrasonic beams.

Since the axial resolution is determined by a pulse width of the ultrasonic signals, the axial resolution is further improved as the ultrasonic signals are high-frequency ultrasonic signals having short pulse widths.

Since the lateral resolution and elevational direction resolution are determined by widths of ultrasonic beams, as the widths of the ultrasonic beams become smaller, the lateral resolution is further improved.

Thus, in order to improve resolution of the ultrasonic image, in particular, to improve the lateral resolution, the ultrasonic signals transmitted from the plurality of transducer elements may be focused on a focal point on a scan line, or the ultrasonic signals received from several imaging points may be focused so that ultrasonic beams having small widths may be formed. This is referred to beamforming.

The ultrasonic diagnostic apparatus 100 in accordance with an embodiment of the present invention may generate reception beams in a desired reception scan line position by employing a synthetic aperture beamforming method, whereby bidirectional dynamic focusing may be performed. Examples of the synthetic aperture beamforming method include a method, whereby, when one transducer element transmits the ultrasonic signals, radio frequency (RF) signals reflected from a target and returned therefrom are received and stored and then, when transmitting/reception of all transducer elements is completed, the stored signals are read and synthesized, a method, whereby the ultrasonic signals are simultaneously transmitted from the plurality of transducer elements, and a method, whereby a transmission focus is assumed as a virtual source element and transmitting/reception focusing is performed at all imaging points by using RF data corresponding to scan lines. In the embodiment of the ultrasonic diagnostic apparatus 100, the synthetic aperture beamforming method is not limited.

Meanwhile, the ultrasonic signals transmitted to an inside of the object pass through a tissue and are deformed. Thus, distortion occurs in waveforms of the ultrasonic signals. Thus, harmonic components together with fundamental components are included in ultrasonic echo signals received by the transducer array 111.

Since the fundamental components are placed in a lower frequency band than that of the harmonic components, the fundamental components have low attenuation in the same medium and are advantageous to watching a deep portion of the image. In the harmonic components, an image including the harmonic components has improved resolution and improved contrast, such as a signal to noise ratio (SNR), compared to that of an image including the fundamental components.

Thus, the ultrasonic diagnostic apparatus 100 in accordance with an embodiment of the present invention extracts the fundamental components and the harmonic components from the ultrasonic echo signals, i.e., the reception beams, and then synthesizes them according to an appropriate ratio, thereby generating an ultrasonic image having both advantages of two components.

As described above, since the ultrasonic diagnostic apparatus 100 in accordance with an embodiment of the present invention employs the synthetic aperture beamforming method, the reception beam generating unit 130 may generate reception beams on a reception scan line in a desired position and may generate reception beams on a reception scan line in a different position from that of a transmission scan line. Thus, the reception beam generating unit 130 generates the reception beams in an appropriate position in consideration of transmission delay of the transmission beams so that the signal processing unit 140 may extract the fundamental components and the harmonic components by using the reception beams.

Figure 3:
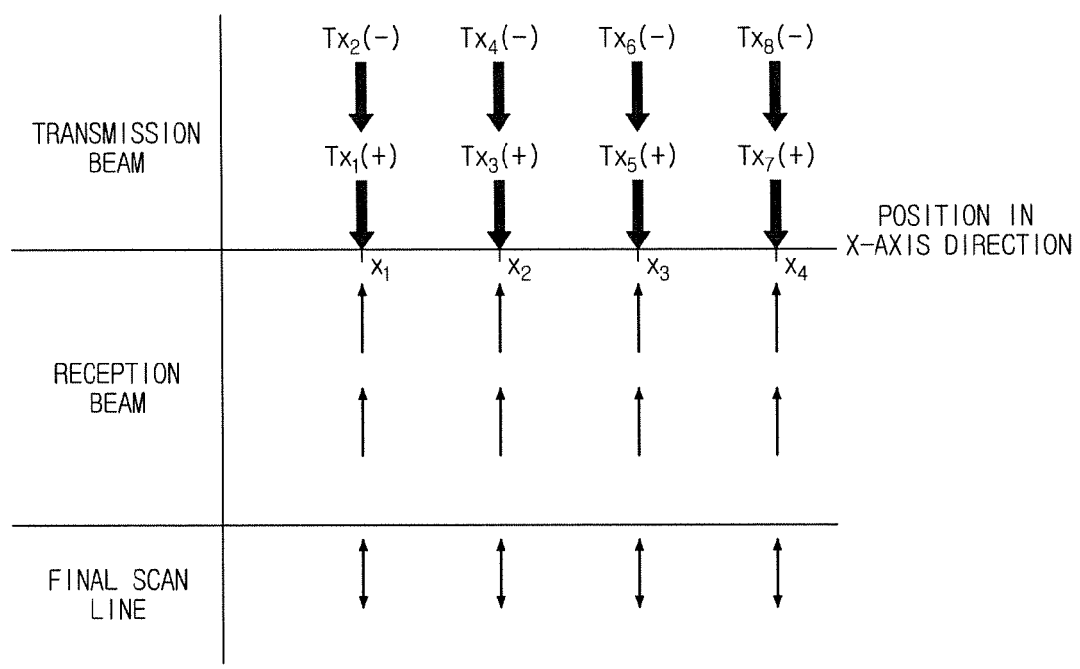
FIG. 3 is a view illustrating relative positions of transmission beams, reception beams, and final scan lines when harmonic components are separated by using an existing pulse inversion method.
Figure 4:
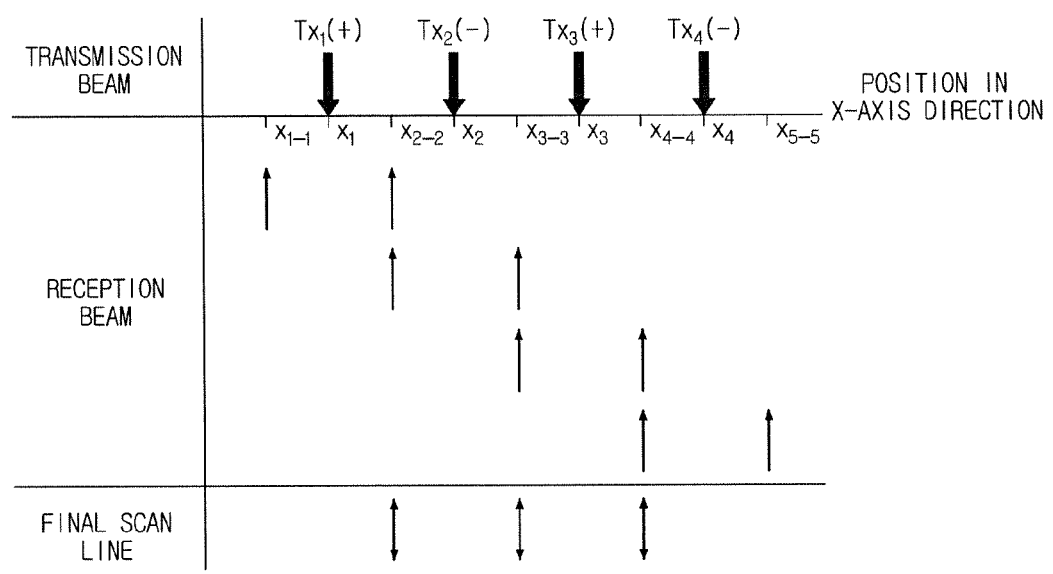
FIG. 4 is a view illustrating relative positions of transmission beams, reception beams, and final scan lines when harmonic components are separated by using the ultrasonic diagnostic apparatus in accordance with an embodiment of the present invention.

FIG. 3 is a view illustrating relative positions of transmission beams, reception beams, and final scan lines when harmonic components are separated by using an existing pulse inversion method, and FIG. 4 is a view illustrating relative positions of transmission beams, reception beams, and final scan lines when harmonic components are separated by using the ultrasonic diagnostic apparatus in accordance with an embodiment of the present invention.

As illustrated in FIG. 3, in an existing method, transmission beams having opposite polarities (a phase difference of 180°) are respectively transmitted to the same position in order to extract harmonic components, and reception beams are added to the transmission beams, so that fundamental components are removed and the harmonic components are emphasized.

In detail, $Tx_1(+)$ and $Tx_2(-)$ are respectively transmitted to a position $x_1$, and a reception beam with respect to $Tx_1(+)$ and a reception beam with respect to $Tx_2(-)$ are added to each other. $Tx_1(+)$ and $Tx_2(-)$ have the same size but have opposite polarities. $Tx_3(+)$ and $Tx_4(-)$ are respectively transmitted to a position $x_2$, and a reception beam with respect to $Tx_3(+)$ and a reception beam with respect to $Tx_4(-)$ are added to each other. In the current embodiment, $Tx_1(+)$ to $Tx_8(-)$ are shown. However, when the number of desired scan lines is n (where n is an integer), 2n reception beams are obtained and added in the same manner. In this case, since transmission beams need to be transmitted twice to the same position, a frame rate is lowered.

In accordance with an embodiment shown in FIG. 4, the transmission beam generating unit 120 generates transmission beams having opposite polarities in different transmission scan line positions and transmits the generated transmission beams to the object by using the transducer module 110. For example, the reception beam generating unit 130 may generate a reception beam with respect to two reception scan line positions offset by a transmission scan line by using the ultrasonic echo signals received from the transducer module 110. Positions of the transmission scan line and the reception scan line may be indicated by positions in the x-axis direction.

In detail, $Tx_1(+)$ is transmitted to the position $x_1$, and $Tx_2(-)$ is transmitted to the position $x_2$, and $Tx_3(+)$ is transmitted to a position $x_3$, and $Tx_4(-)$ is transmitted to a position $x_4$. That is, transmission beams having frequencies of opposite polarities are alternately transmitted to different transmission scan line positions. The transmission beams transmitted to respective positions may have the same size.

The reception beam generating unit 130 generates a reception beam with respect to $Tx_1(+)$ in positions $x_{1-1}$ and $x_{2-2}$ and generates a reception beam with respect to $Tx_2(-)$ in positions $x_{2-2}$ and $x_{3-3}$. The reception beam generating unit 130 generates a reception beam with respect to $Tx_3(+)$ in positions $x_{3-3}$ and $x_{4-4}$ and generates a reception beam with respect to $Tx_4(+)$ in positions $x_{4-4}$ and $x_{5-5}$.

As a result, reception beams having different polarities are generated in the same reception scan line position. Thus, the reception beams are added so that signals from which fundamental components are removed, may be obtained.

Thus, the ultrasonic diagnostic apparatus 100 in accordance with an embodiment of the present invention does not remove the fundamental components by using simple filtering and thus may extract second harmonic components, amplitudes of which are improved, and does not repeatedly radiate the transmission beams onto the same transmission scan line position so that the frame rate may not be lowered.

Figure 5:
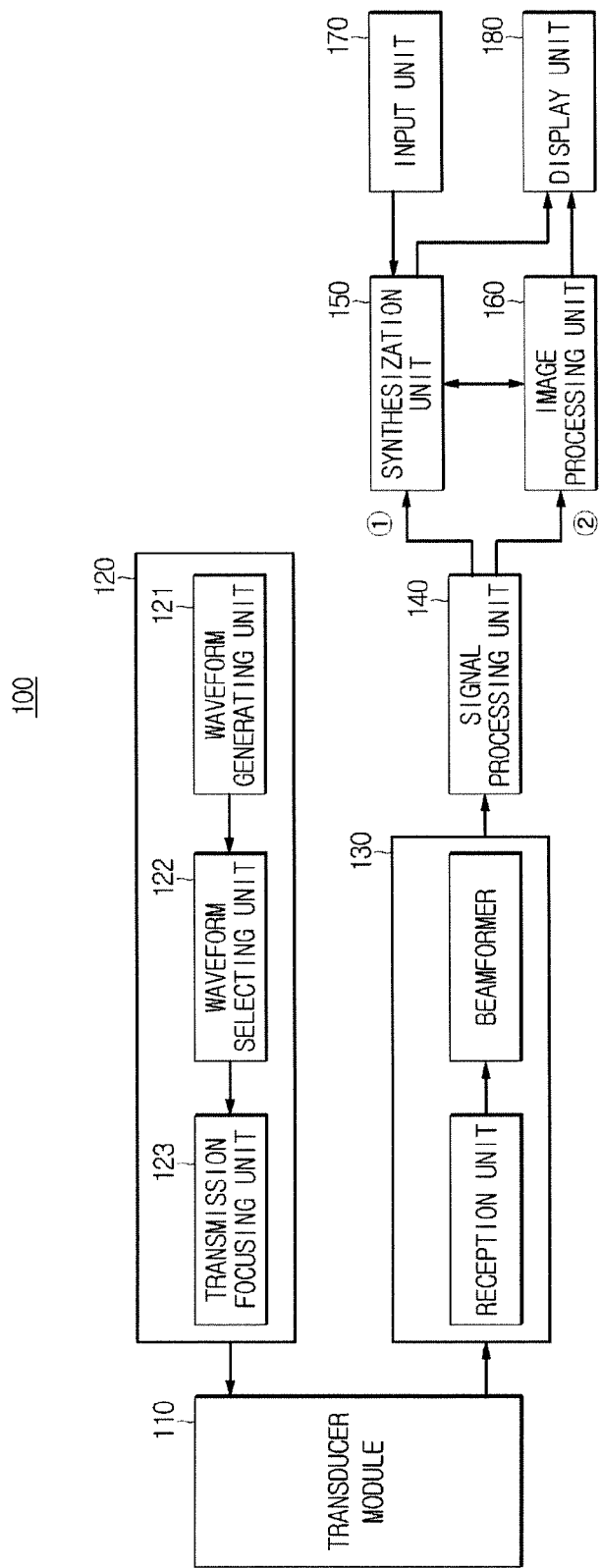
FIG. 5 is a control block diagram of concretized configurations of a transmission beam generating unit and a reception beam generating unit.

FIG. 5 is a control block diagram of concretized configurations of a transmission beam generating unit and a reception beam generating unit.

Referring to FIG. 5, the transmission beam generating unit 120 may include a waveform generating unit 121 that generates waveforms of transmission signals with respect to transmission scan lines, a waveform selecting unit 122 that selects waveforms to be transmitted to the transducer elements, and a transmission focusing unit 123 that focuses the transmission signals to be transmitted to the transducer element.

The waveform generating unit 121 generates waveforms having appropriate frequency and phase suitable for characteristics of the object and a diagnostic purpose. In this case, the waveform generating unit 121 may generate waveforms according to a combination in which the sum of waveforms may be 0. For example, two waveforms having a phase difference of 180° may be set to one set, and four waveforms having a phase difference of 90° may be set to one set.

The waveform selecting unit 122 selects waveforms to be transmitted to the transducer elements in respective transmission scan line positions. For example, when two waveforms having the phase difference of 180° is set to one set, two waveforms having the phase difference of 180° may be selected and transmitted to the transducer elements corresponding to two consecutive transmission scan lines. In this case, a transducer element corresponding to one transmission scan line may be provided as one transducer element or in the plural according to a transmission focusing method.

When a plurality of transducer elements corresponding to one transmission scan line are provided, the transmission focusing unit 123 gives time delay so that the ultrasonic signals transmitted from the transducer elements may simultaneously reach a focal point on a transmission scan line, thereby generating transmission beams. When widths of ultrasonic beams are reduced by focusing the ultrasonic signals, the lateral resolution may be improved.

The transducer module 110 receives ultrasonic echo signals, converts the ultrasonic echo signals into electrical signals, and transmits the electrical signals to the reception beam generating unit 130. In the following embodiment that will be described below, the ultrasonic echo signals converted into the electrical signals are referred to as reception signals.

The reception beam generating unit 130 may include a reception unit 131 that performs amplification and gain correction by receiving the reception signals, and a beamformer 132 that generates reception beams corresponding to the transmission beams by using the reception signals.

Also, when the beamformer 132 is implemented with a digital beamformer, the reception unit 131 may further include an analog-to-digital converter (ADC) and may convert analog reception signals on which amplification and gain correction are performed, into digital reception signals.

The beamformer 132 generates reception beams in desired reception scan line positions by using the reception signals. In detail, the beamformer 132 generates reception beams with respect to different transmission beams in the same reception scan line position. Here, different transmission beams that are transmission beams radiated onto different transmission scan lines, refer to transmission beams in which the sum of waveforms is 0.

The ultrasonic diagnostic apparatus 100 in accordance with an embodiment of the present invention employs the synthetic aperture beamforming method and thus may generate reception beams with respect to reception scan lines in different positions from those of transmission scan lines. Thus, as illustrated in FIG. 4 described above, the beamformer 132 may generate reception beams with respect to at least two reception scan line positions offset by the transmission scan line positions when generating reception beams with respect to one transmission beam. For example, the beamformer 132 may generate a reception beam with respect to $Tx_1(+)$ and a reception beam with respect to $Tx_2(-)$ in the position $x_{2-2}$.

However, as illustrated in FIG. 4, generating two reception scan lines offset by one transmission scan line position is merely one embodiment of the ultrasonic diagnostic apparatus 100. The beamformer 132 may generate three or more reception scan lines or one reception scan line with respect to one transmission scan line position according to a combination of transmission beam sets and may generate reception scan lines in the same position as that of transmission scan lines.

Figure 6:
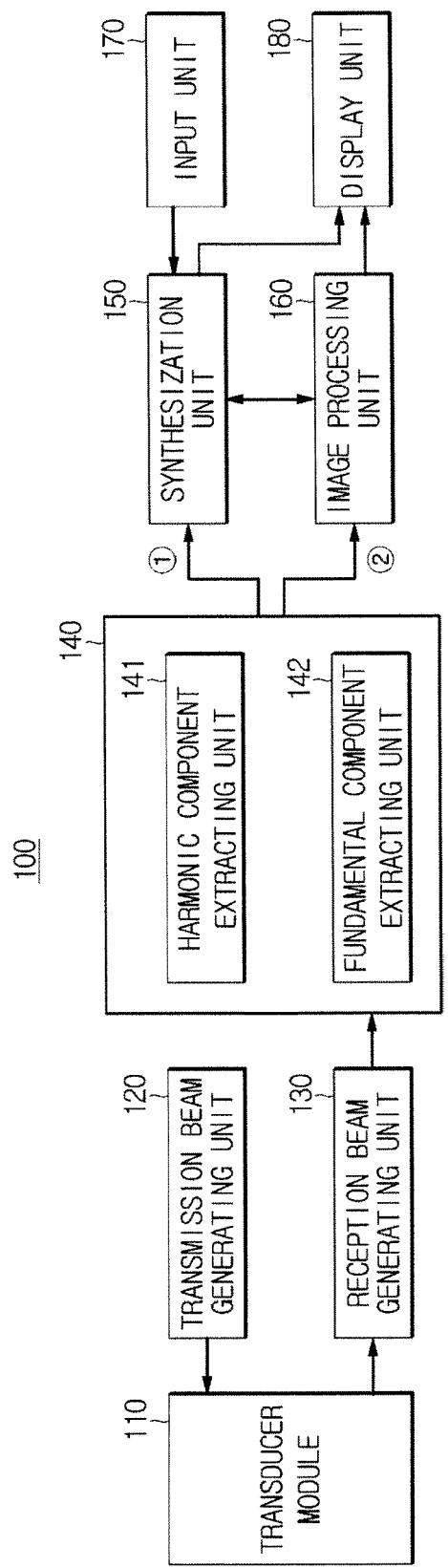
FIG. 6 is a control block diagram of a concretized configuration of a signal processing unit.

FIG. 6 is a control block diagram of a concretized configuration of a signal processing unit, and FIGS. 7A and 7B are views for describing extraction of harmonic components and fundamental components, and FIGS. 8A and 8B through 10A and 10B are views of signal modeling of reception beams.

Referring to FIG. 6, the signal processing unit 140 may include a harmonic component extracting unit 141 and a fundamental component extracting unit 142. The harmonic component extracting unit 141 extracts harmonic components from reception beams, and the fundamental component extracting unit 142 extracts fundamental components from the reception beams. Both the harmonic components and the fundamental components refer to frequency components.

The harmonic component extracting unit 141 and the fundamental component extracting unit 142 may extract the harmonic components and the fundamental components respectively by coupling the reception beams generated in the same reception scan line position. Here, coupling may be summation or subtraction of signals, or a combination thereof.

As illustrated in FIG. 7A, the harmonic component extracting unit 141 may extract harmonic components $H_1$ obtained by removing fundamental components from reception beams $Rx_1(+)$ and $Rx_2(-)$ generated in the position $x_{2-2}$ by summing up the reception beams $Rx_1(+)$ and $Rx_2(-)$ generated in the position $x_{2-2}$ and may extract harmonic components $H_2$ obtained by removing fundamental components from reception beams $Rx_2(-)$ and $Rx_3(+)$ generated in the position $x_{3-3}$ by summing up the reception beams $Rx_2(-)$ and $Rx_3(+)$ generated in the position $x_{3-3}$. The harmonic component extracting unit 141 may extract harmonic components $H_3$ obtained by removing fundamental components from reception beams $Rx_3(+)$ and $Rx_4(-)$ generated in the position $x_{4-4}$ by summing up the reception beams $Rx_3(+)$ and $Rx_4(-)$ generated in the position $x_{4-4}$. Thus, final scan lines may be generated in the positions $x_{2-2}$, $x_{3-3}$, and $x_{4-4}$. Here, summation performed on the reception beams may be coherent summation.

In the current embodiment, for conveniences of explanation, the harmonic components $H_1$ to $H_3$ have been described. However, the same method may be applied to scan lines after the harmonic components $H_3$.

As illustrated in FIG. 7B, the fundamental component extracting unit 142 may extract fundamental components $F_1$ by summing up the reception beam $Rx_1(+)$ generated in the position $x_{2-2}$ and a reception beam $-Rx_2(-)$ obtained by adding a negative sign (−) to $Rx_2(-)$. In other words, the fundamental component extracting unit 142 may extract the fundamental component $F_1$ obtained by removing harmonic components by subtracting $Rx_2(-)$ from $Rx_1(+)$. The fundamental component extracting unit 142 may extract fundamental components $F_2$ obtained by removing harmonic components by summing up the reception beams $Rx_3(+)$ and $-Rx_2(-)$ generated in the position $x_{3-3}$, and may extract fundamental components $F_3$ by summing up the reception beams $Rx_3(+)$ and $-Rx_4(-)$ generated in the position $x_{4-4}$. That is, the fundamental component extracting unit 142 may extract the fundamental components obtained by removing the harmonic components, by summing up the reception beams generated in the same reception scan line position after adding a negative sign to a reception beam generated with respect to a transmission beam having a negative (−) polarity. Even in this case, final scan lines may be generated in the positions $X_{2-2}$, $X_{3-3}$, and $X_{4-4}$.

Figure 8A:
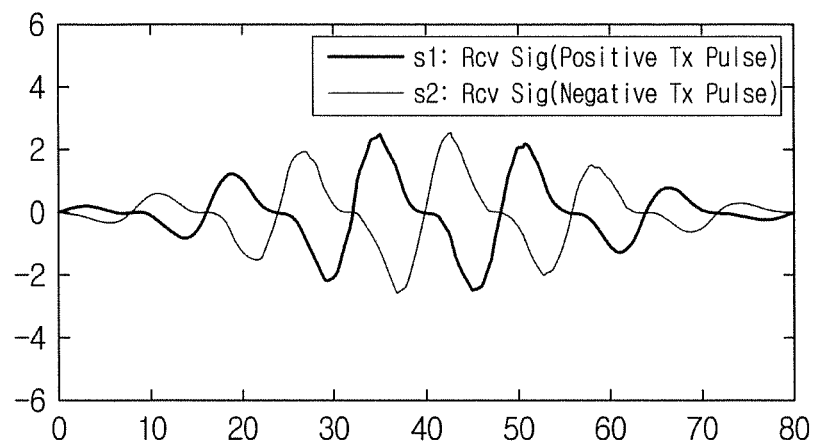
Figure 8B:
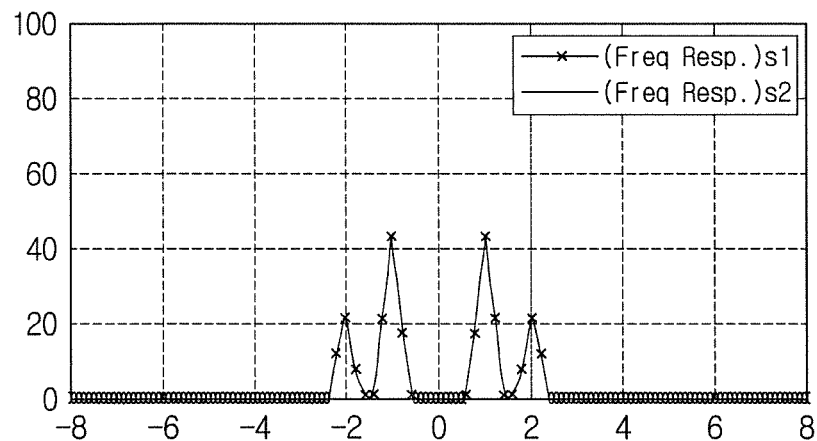

The relationship between frequencies and amplitudes of a reception signal s1 corresponding to a transmission beam having a positive polarity and a reception signal s2 corresponding to a transmission beam having a negative polarity is as illustrated in FIG. 8A. Also, frequency response characteristics of two reception signals s1 and s2 are as illustrated in FIG. 8B.

Figure 9A:
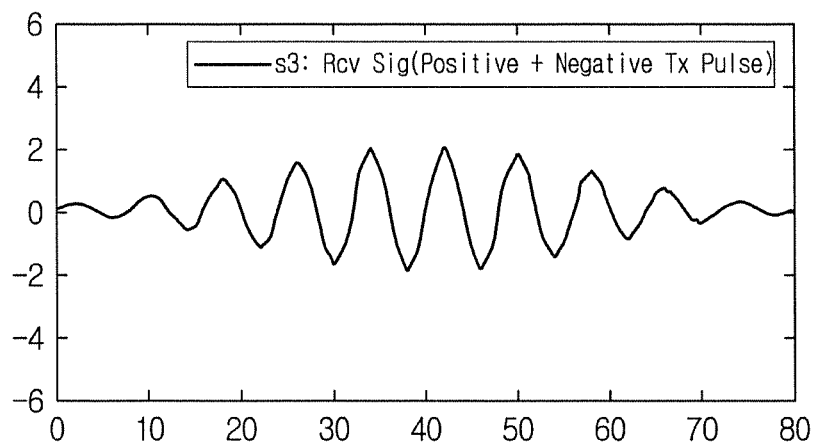

The relationship between a frequency and an amplitude of a signal (s3=s1+s2) obtained by summing up two reception signals s1 and s2 by using the harmonic component extracting unit 141 is as illustrated in FIG. 9A. The signal s3 is a harmonic signal from which fundamental components are removed and of which harmonic components are emphasized, and in particular, corresponds to a second harmonic signal.

Figure 9B:
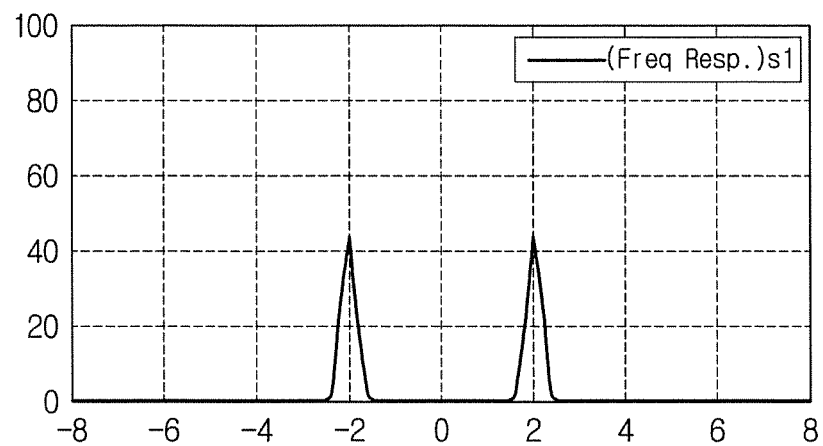

A frequency response of the second harmonic signal s3 may be indicated by a graph shown in FIG. 9B. Here, it may be checked that fundamental components are removed from the second harmonic signal s3.

Figure 10A:
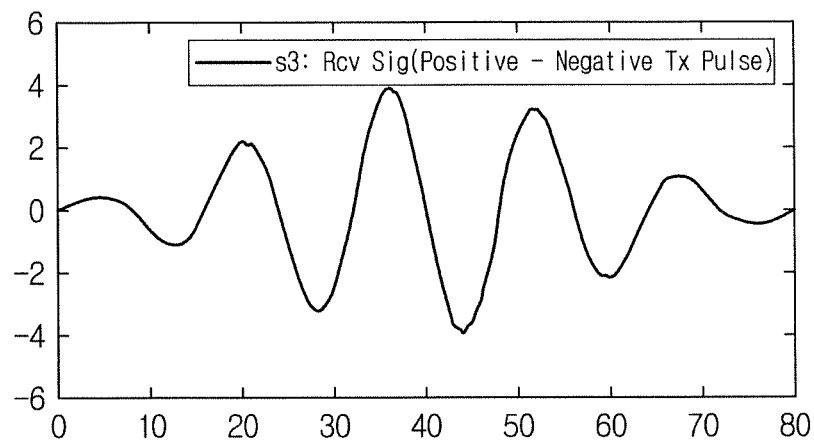

The relationship between a frequency and an amplitude of a signal (s4=s1−s2) obtained by subtracting two reception signals s1 and s2 by using the fundamental component extracting unit 142 is as illustrated in FIG. 10A. The signal s4 is a fundamental signal from which harmonic components are removed and of which fundamental components are emphasized.

Figure 10B:
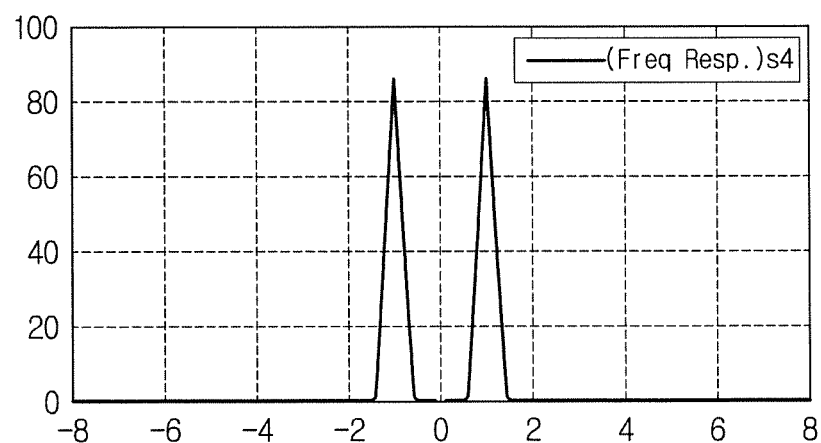

A frequency response of the fundamental signal s4 may be indicated by a graph shown in FIG. 10B. Here, it may be checked that harmonic components are removed from the fundamental signal s4.

In the above-described embodiment, a transmission beam set includes two transmission beams having a phase difference of 180°. As another example, transmission beams shifted by 90°, such as $s_1=\cos(\theta)$, $s_2=\cos(\theta+\pi/2)$, $s_3=\cos(\theta+\pi)$, and $s_4=(\theta+3\pi/2)$, may be set to one transmission beam set. In this case, the harmonic component extracting unit 141 may extract harmonic components by coherently summing up a reception beam $Rx\_s_1$ corresponding to $s_1$, a reception beam $Rx\_s_2$ corresponding to $s_2$, a reception beam $Rx\_s_3$ corresponding to $s_3$, and a reception beam $Rx\_s_4$ corresponding to $s_4$.

Also, the fundamental component extracting unit 142 may extract fundamental components by calculating $(Rx\_s_1-Rx\_s_3)$, $(Rx\_s_2-Rx\_s_4)$, or $((Rx\_s_1 Rx\_s_3)+(Rx\_s_2-Rx\_s_4))$.

The embodiment of the ultrasonic diagnostic apparatus 100 is not limited to the examples, and a case where transmission beams in which the sum of waveforms is 0, may be set to one set and fundamental components or harmonic components may be removed by properly coupling the reception beams corresponding to the transmission beams, may be applied to the embodiment of the ultrasonic diagnostic apparatus 100.

Figure 11:
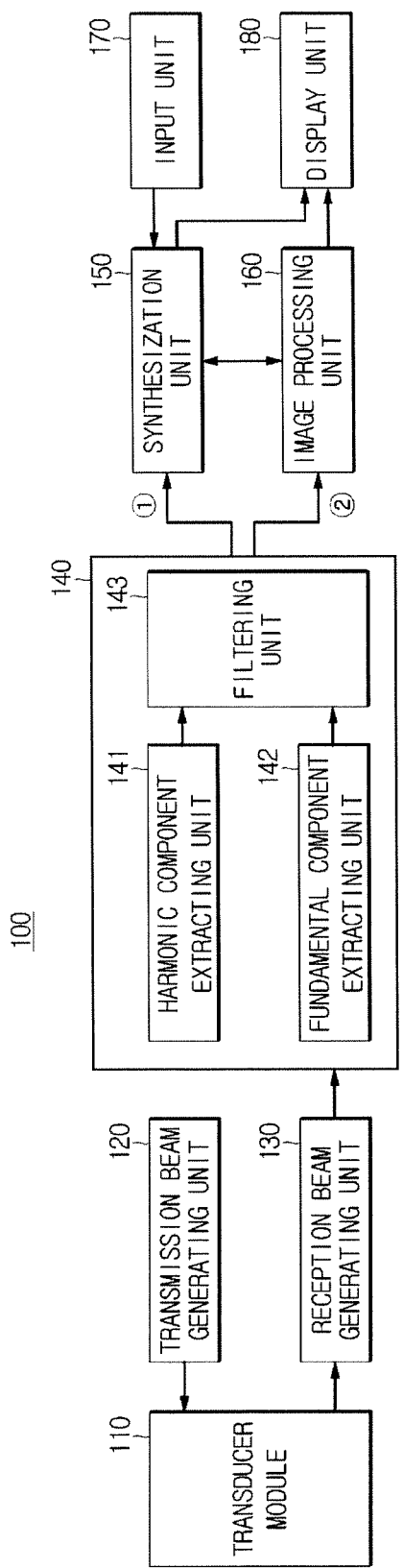
FIG. 11 is a control block diagram of the ultrasonic diagnostic apparatus that performs filtering on the fundamental components and the harmonic components.
Figure 12B:
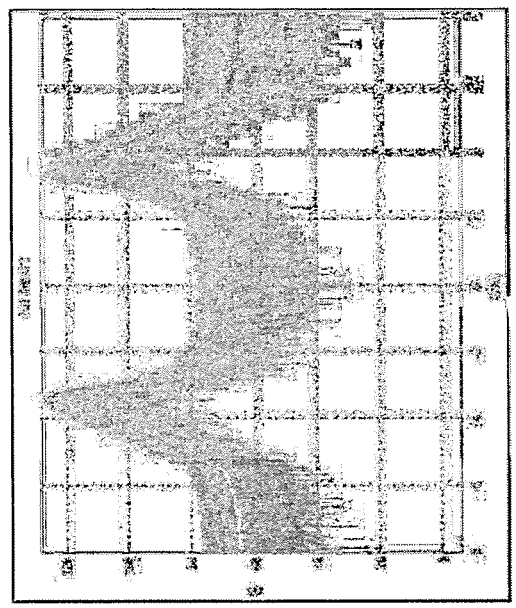
FIGS. 12A and 12B are graphs showing the result of filtering on the harmonic components.
Figure 12A:
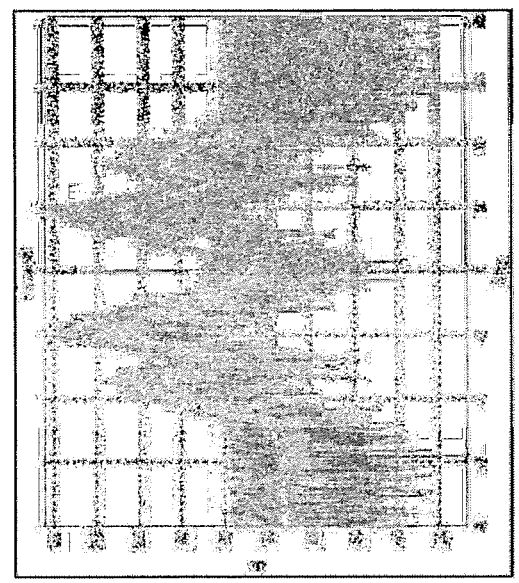

FIG. 11 is a control block diagram of the ultrasonic diagnostic apparatus that performs filtering on the fundamental components and the harmonic components, and FIGS. 12A and 12B are graphs showing the result of filtering on the harmonic components, and FIGS. 13A and 13B are graphs showing the result of filtering on the fundamental components.

Referring to FIG. 11, the ultrasonic diagnostic apparatus 100 may further include a filtering unit 143 that performs filtering on the harmonic components extracted by the harmonic component extracting unit 141 and on the fundamental components extracted by the fundamental component extracting unit 142.

As illustrated in FIG. 12A, various noise in addition to the harmonic components may be included in the harmonic components extracted by the harmonic component extracting unit 141. Thus, the filtering unit 143 may perform filtering by applying a filter, such as a low pass filter (LPF), to the harmonic components, thereby obtaining harmonic signals from which noise is removed, as illustrated in FIG. 12B. Also, the filtering unit 143 may perform a function of demodulation in which signals are lowered to a baseband by filtering so as to restore actual signals.

Also, as illustrated in FIG. 13A, various noise in addition to the fundamental components may be included in the fundamental components extracted by the fundamental component extracting unit 142. Thus, the filtering unit 143 may perform filtering by applying a filter, such as an LPF, onto the fundamental components, thereby obtaining fundamental signals from which noise is removed, as illustrated in FIG. 13B.

The filtering unit 143 may perform filtering on both the harmonic components and the fundamental components and may perform filtering only on one of the harmonic components and the fundamental components if necessary. Also, a different filter, such as a quadrature bandpass filter (QBP), may be applied, in addition to the LPF, and a filter and a mixer may be used together. In the embodiment of the ultrasonic diagnostic apparatus 100, the type of the filter is not limited.

Figure 14:
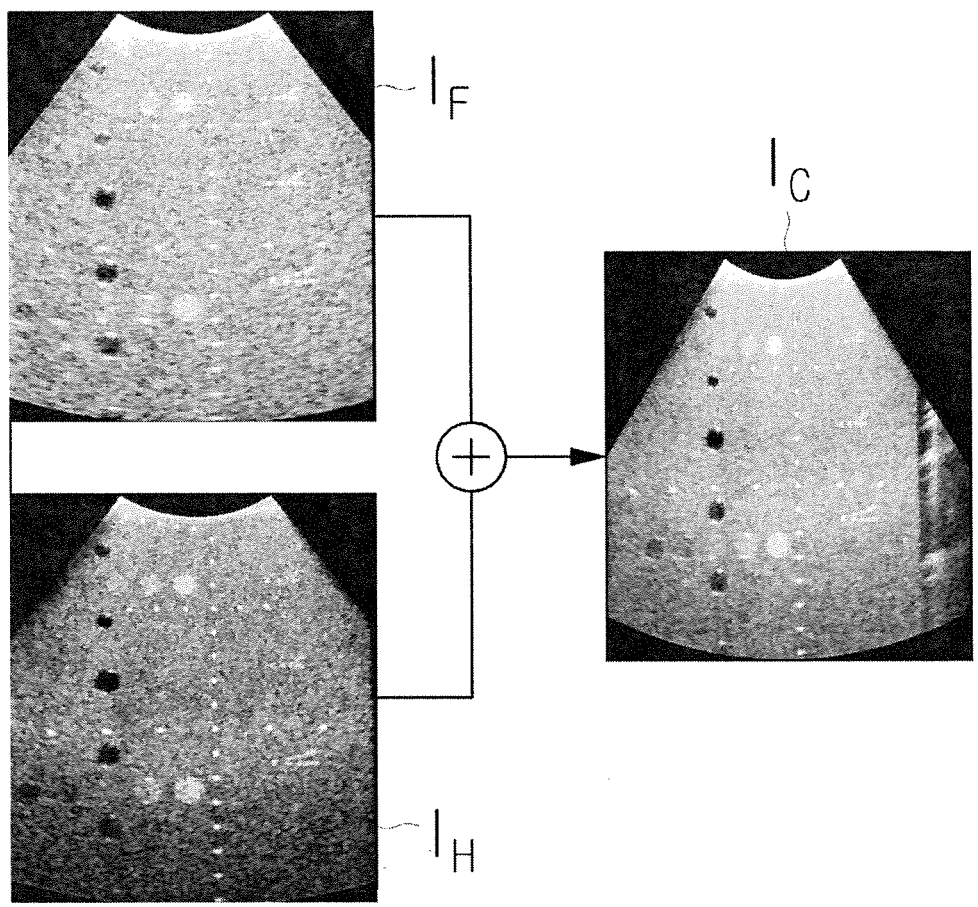
FIG. 14 is a view of an operation of synthesizing a harmonic image and a fundamental image by using a synthesization unit.

FIG. 14 is a view of an operation of synthesizing a harmonic image and a fundamental image by using a synthesization unit.

As illustrated in FIG. 14, the synthesization unit 150 may generate a synthesized image $I_C$ by synthesizing a harmonic image $I_H$ and a fundamental image $I_F$ according to an appropriate synthesization ratio. To this end, the harmonic image $I_H$ and the fundamental image $I_F$ need to be generated. The image processing unit 160 may generate a fundamental image and a harmonic image by performing processing, such as compression, spatial filtering, temporal filtering, or discrete singular convolution (DSC), on the fundamental components and the harmonic components. Also, the image processing unit 160 may perform various filtering on the synthesized image.

The synthesization unit 150 may generate the synthesized image $I_C$ by providing appropriate weighted values to the harmonic image $I_H$ and the fundamental image $I_F$ and then synthesizing them. In this case, the synthesization unit 150 may perform weighted value synthesization in the entire region, or synthesization by providing different weighted values according to regions, or may perform weighted value synthesization only in a particular region.

For example, when a synthesization ratio of the fundamental image $I_F$ is 100% and a synthesization ratio of the harmonic image $I_H$ is 0%, the fundamental image $I_F$ is a synthesized image, and in an inverse case, the harmonic image $I_H$ is the synthesized image. Also, when the sythesization ratio of the fundamental image $I_F$ is 40% and the synthesization ratio of the harmonic image $I_H$ is 60%, a synthesized image may be generated by applying a corresponding synthesization ratio to each image.

When the synthesized image is generated, the fundamental image and the harmonic image may be synthesized, as described above, and after the fundamental components and the harmonic components are synthesized, the synthesized image may be generated by performing image processing on a synthesized signal. That is, an image itself may be synthesized to generate the synthesized image, and image processing may be performed on a synthesized frequency after frequency components are synthesized.

Referring back to FIG. 1, when the image itself is synthesized, i.e., when the fundamental image and the harmonic image are synthesized, the fundamental components and the harmonic components that correspond to an output of the signal processing unit 140 according to a flow ② are first input to the image processing unit 160, are converted into a fundamental image and a harmonic image, and then are input to the synthesization unit 150. The synthesization unit 150 may generate a synthesized image by synthesizing two images according to an appropriate synthesization ratio, as described above.

When the frequency components are synthesized, i.e., when the fundamental components and the harmonic components are synthesized, the fundamental components and the harmonic components corresponding to an output of the signal processing unit 140 may be input to the synthesization unit 150 according to a flow ① and may be synthesized according to the appropriate synthesization ratio. Synthesized signals may be input to the image processing unit 160, and the image processing unit 160 may generate the synthesized image by performing image processing on the synthesized signals. The synthesized image refers to an ultrasonic image regarding the synthesized signals.

In accordance with an embodiment of the ultrasonic diagnostic apparatus 100, a synthesized image in which fundamental components and harmonic components are included, is generated and is used in imaging without attenuating the fundamental components so that an ultrasonic image having frequency characteristics of a broad band may be obtained.

A synthesization ratio of the fundamental components and the harmonic components may be set by the synthesization unit 150 or input from a user.

When the synthesization unit 150 sets the synthesization ratio, the synthesization unit 150 may set the synthesization ratio according to characteristics of the extracted fundamental components and harmonic components, according to the object or a diagnostic purpose or in consideration of both of them, or according to a previously-designed algorithm. An embodiment of a case where the synthesization ratio is input from the user, will be described later.

When an operation of separating fundamental components and harmonic components from reception beams or an operation of synthesizing two components may be performed continuously with reception of received signal, but extraction or synthesization of two components may also be performed with a time difference after the reception beams have been previously obtained.

Figure 15:
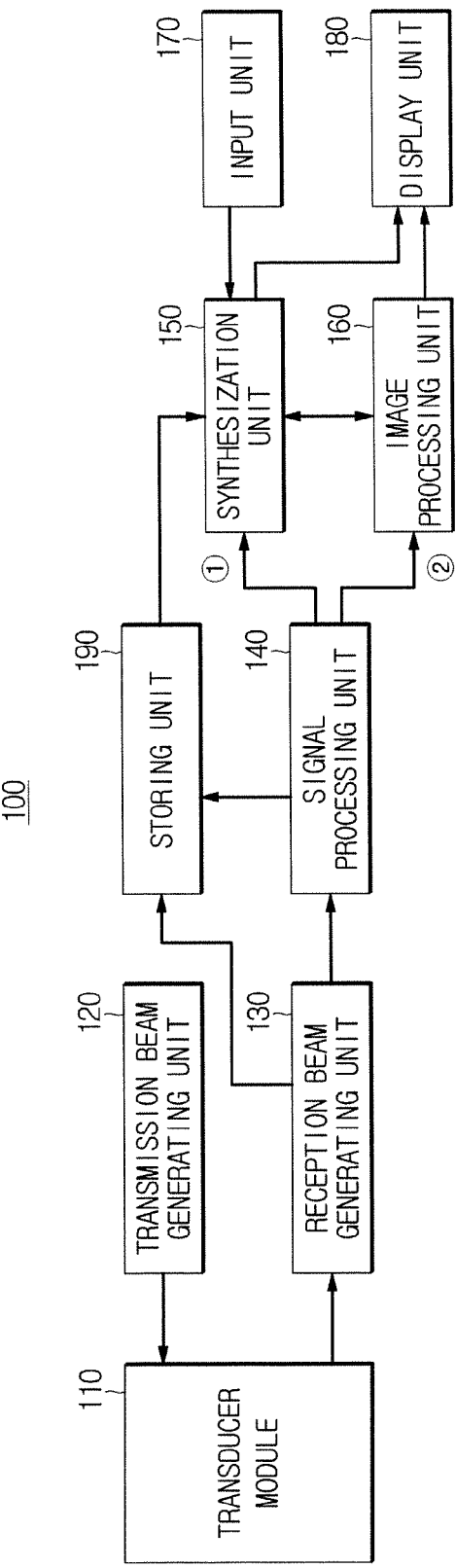
FIG. 15 is a control block diagram of the ultrasonic diagnostic apparatus further including a storing unit.

FIG. 15 is a control block diagram of the ultrasonic diagnostic apparatus further including a storing unit.

The ultrasonic diagnostic apparatus 100 in accordance with an embodiment of the present invention may further include a storing unit 190 that stores reception beams or extracted fundamental components or harmonic components.

When extraction of the fundamental components and the harmonic components is performed after the reception beams are obtained, the reception beams stored in the storing unit 190 may be called, and the signal processing unit 140 may extract the fundamental components and the harmonic components from the stored reception beam.

Alternatively, when synthesization is performed on the fundamental components and the harmonic components that have been previously separated from each other, the fundamental components and the harmonic components stored in the storing unit 190 may be called, and the synthesization unit 150 may synthesize two components according to an appropriate synthesization ratio.

The storing unit 190 may be implemented with a nonvolatile memory device, such as read only memory (ROM), programmable read only memory (PROM), erasable programmable read only memory (EPROM), or flash memory, a volatile memory device, such as random access memory (RAM), or a storing device, such as a hard disk or an optical disc. However, embodiments of the present invention are not limited thereto, and the storing unit 190 may also be implemented with an arbitrary different shape known to one of ordinarily skill in the art.

Figure 16:
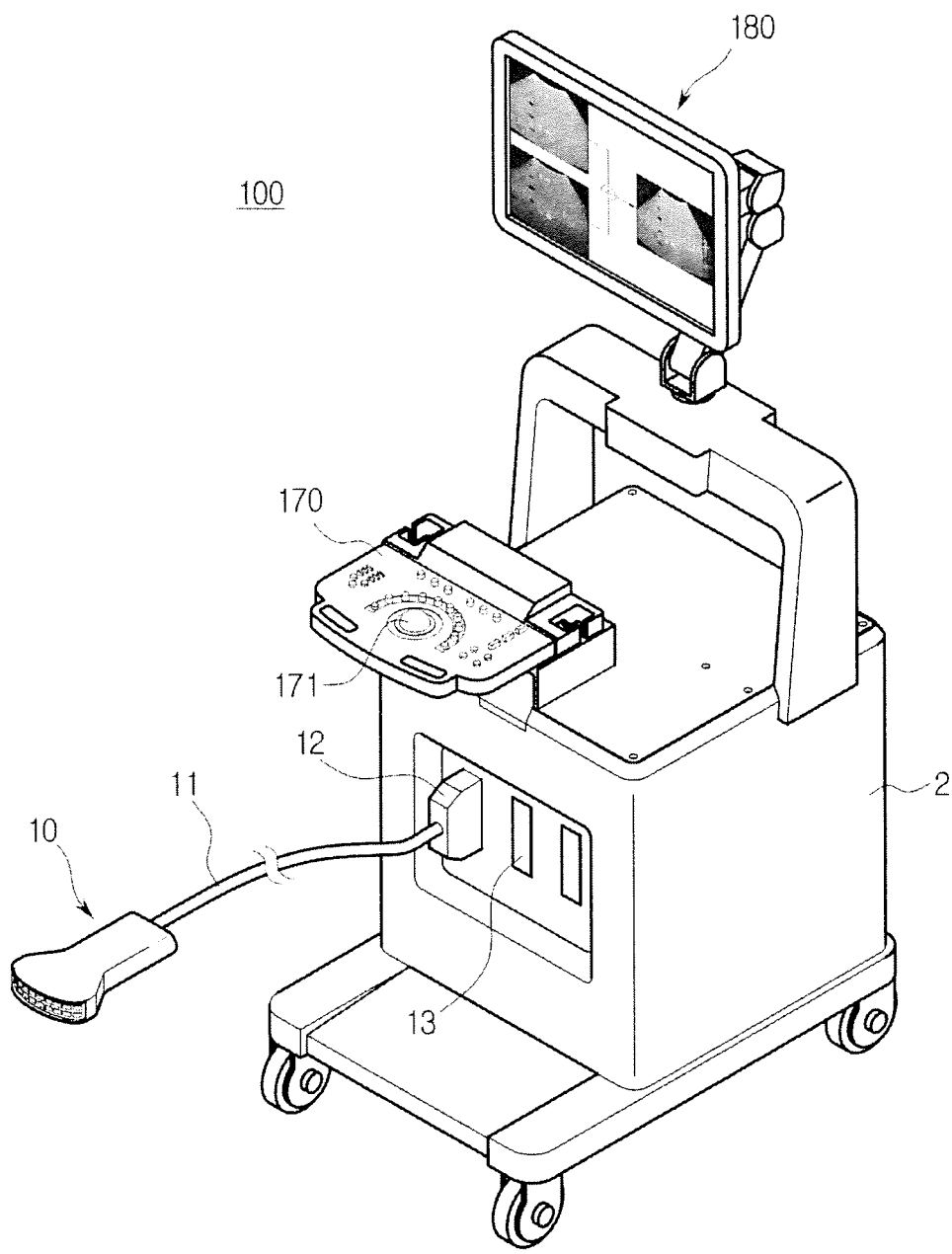
FIGS. 16 and 17 are views of an exterior of the ultrasonic diagnostic apparatus in accordance with an embodiment of the present invention.
Figure 17:
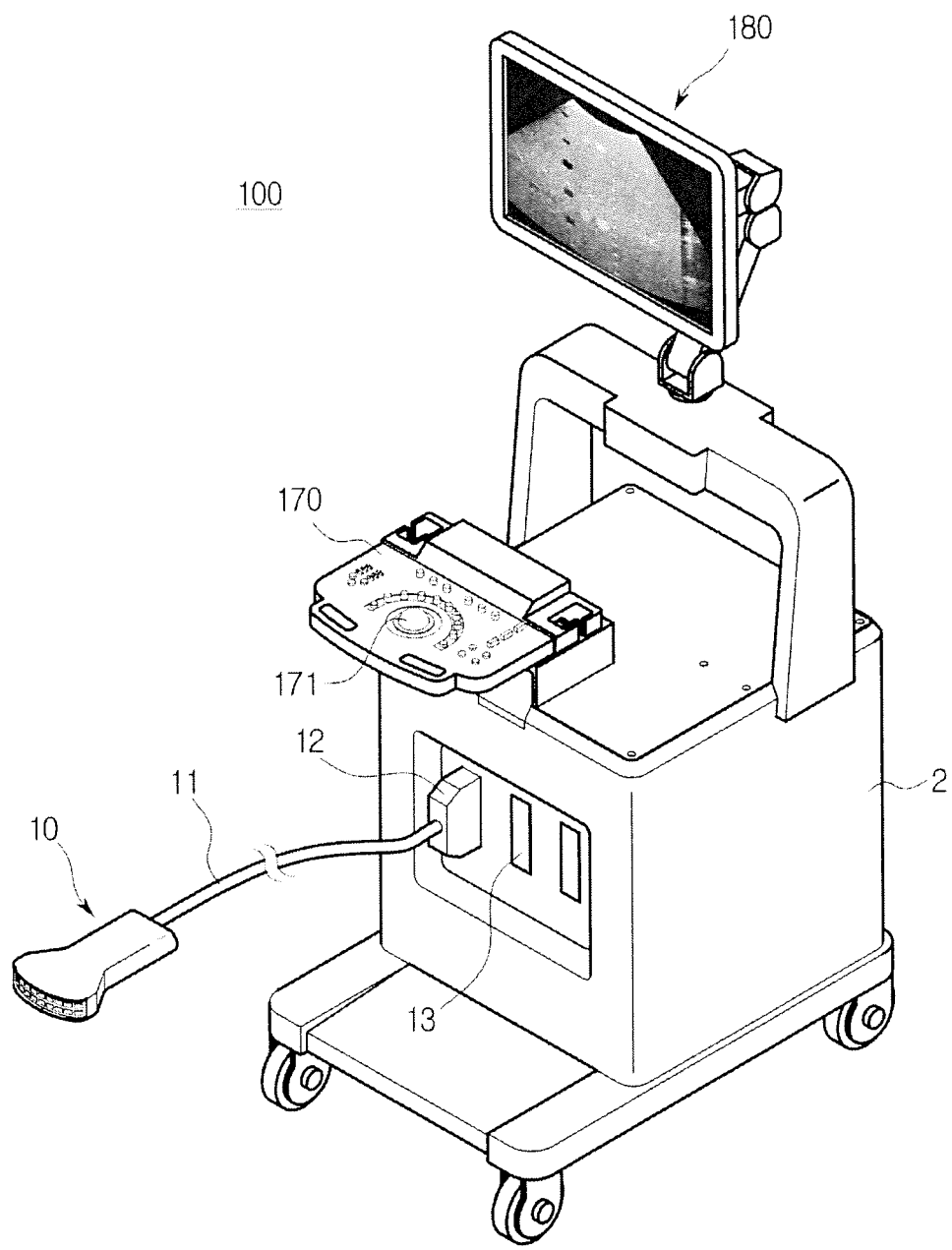

FIGS. 16 and 17 are views of an exterior of the ultrasonic diagnostic apparatus in accordance with an embodiment of the present invention.

When the synthesization ratio is input from the user, as illustrated in FIGS. 16 and 17, the user's selection may be input to the input unit 170 disposed in the ultrasonic diagnostic apparatus 100. Hereinafter, an operation in which the synthesization ratio is selected by the input unit 170, will be described with reference to FIGS. 16 and 17 together with the exterior of the ultrasonic diagnostic apparatus 100.

Referring to FIGS. 16 and 17, the ultrasonic diagnostic apparatus 100 may include a probe 10 connected to a main body 2 through a cable 11. An end of one side of the cable 11 may be connected to the probe 10, and a connector 12 may be disposed on an end of the other side of the cable 11 so as to be coupled to or separated from a slot 7 of the main body 2. Control instructions or data may be exchanged between the main body 2 and the probe 10 by using the cable 11.

Alternatively, when the probe 10 is implemented with a wireless probe, the probe 10 and the main body 2 may be connected to each other via a wireless network (not via the cable 11).

The transducer module 110 may be included in the probe 10. Also, according to an implementation example of the ultrasonic diagnostic apparatus 100, a part or the whole of elements of the transmission beam generating unit 120 may be included in the probe 10, and a part or the whole of elements of the reception beam generating unit 130 may also be included in the probe 10.

The input unit 170 to which the user's control instructions are input, and the display unit 180 that displays a screen required to receive the control instructions of the ultrasonic diagnostic apparatus 100 from the user, may be disposed in the main body 2.

The input unit 170 may be implemented with at least one of various input devices, such as a jog shuttle, a track ball, a button, and a mouse and may also be implemented with a touch panel.

The display unit 180 may be implemented with at least one among various display devices, such as a liquid crystal display (LCD), a light emission diode (LED), a plasma display panel (PDP), and an organic light emission diode (OLED).

The user may input a synthezation ratio of fundamental components and synthesization components by manipulating the input unit 170. In this case, as illustrated in FIG. 16, the display unit 180 may display a fundamental image including the fundamental components and a harmonic image including the harmonic components, and the user may select the synthesization ratio by referring to the displayed fundamental image and harmonic image. In this case, the user may select synthesization ratios with respect to a lateral direction, an axial direction, and an elevational direction, respectively, and the input unit 170 may be separately disposed in each of the directions.

Also, a synthesized image synthesized according to the synthesization ratio selected by the user may be together displayed in one region of the display unit 180 so that the user's selection may be assisted. Before the user determines the synthesization ratios, the displayed synthesized image may be changed according to the synthesization ratio that changes when the user manipulates the input unit 170.

Alternatively, as illustrated in FIG. 17, the display unit 180 may not display the fundamental image and the harmonic image but only the synthesized image so that the user's selection may be assisted.

Also, although not shown, the display unit 180 may visualize the synthesization ratio of two components quantitatively. For example, the synthesization ratio corresponding to the user's current manipulation may be displayed by numbers or graphs, or in a bar shape. When the input unit 170 is implemented with track balls or a jog shuttle, the user may check the selected synthesization ratio while manipulating the input unit 170 by using information displayed on the display unit 180.

Hereinafter, an embodiment of a method of controlling the ultrasonic diagnostic apparatus 100 will be described. When the method of controlling the ultrasonic diagnostic apparatus 100 is performed, the ultrasonic diagnostic apparatus 100 according to the above-described embodiment may be used. Thus, a description of the above-described embodiment of the ultrasonic diagnostic apparatus 100 may also be applied to the method of controlling the ultrasonic diagnostic apparatus 100.

Figure 18:
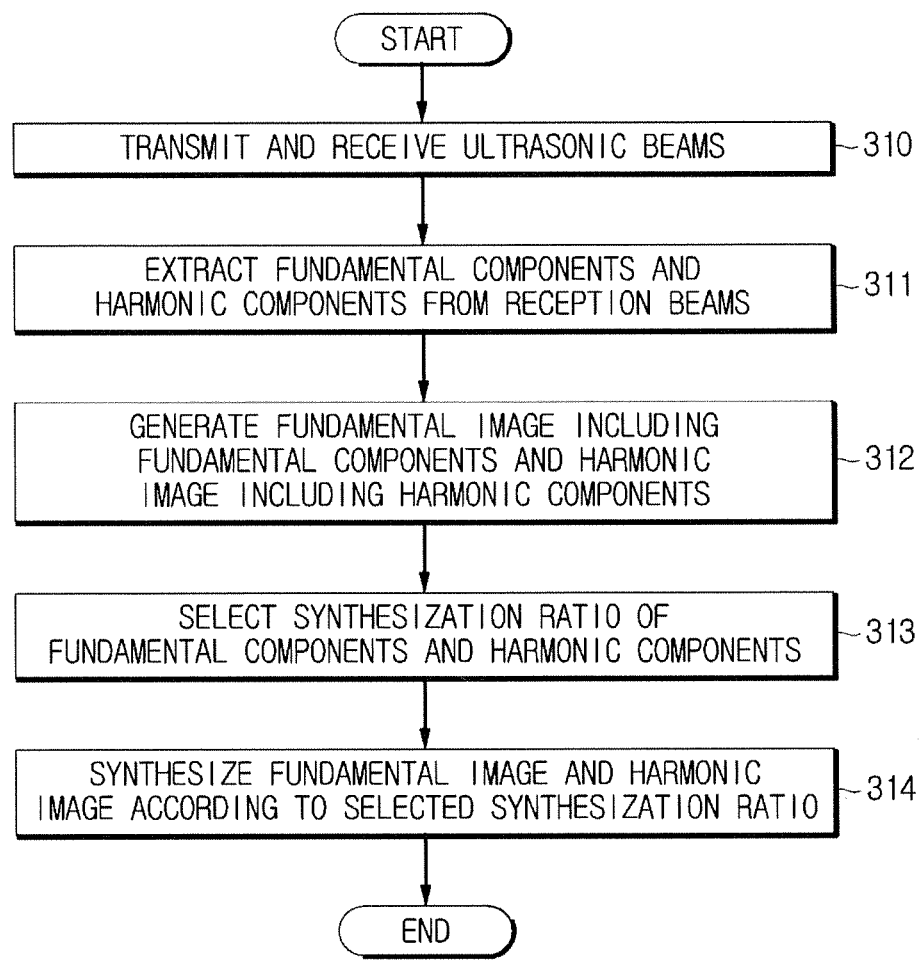
FIG. 18 is a flowchart of a method of controlling the ultrasonic diagnostic apparatus, in accordance with an embodiment of the present invention.

FIG. 18 is a flowchart of a method of controlling the ultrasonic diagnostic apparatus, in accordance with an embodiment of the present invention.

Referring to FIG. 18, ultrasonic beams are transmitted and received (310).

A synthetic aperture beamforming method, whereby bidirectional dynamic focusing may be performed, may be employed to transmit and receive the ultrasonic beams. As illustrated in FIG. 4 described above, the transmission beam generating unit 120 may generate transmission beams in all transmission scan lines by setting the transmission beams in which the sum of waveforms is 0, to one set. When the transmission beams are radiated by the transducer module 110, the reception beam generating unit 130 may generate reception beams in positions of at least two reception scan lines offset by transmission scan lines. When transmission and reception of the ultrasonic beams are repeatedly performed in the same manner, reception beams with respect to the transmission beams having different polarities are generated in the same reception scan line position.

Fundamental components and harmonic components are extracted from the reception beams (311).

As described above, the reception beams with respect to the transmission beams having different polarities are generated in the same reception scan line position by transmission and reception of the ultrasonic beams. As illustrated in FIG. 7 described above, the signal processing unit 140 may extract the harmonic components obtained by removing the fundamental components from the reception beams, by summing up the reception beams in the same reception scan line position. Also, the fundamental components obtained by removing the harmonic components from the reception beams, may be extracted by subtracting the reception beams in the same reception scan line position.

A fundamental image including the fundamental components and a harmonic image including the harmonic components are generated by performing image processing (312).

The image processing unit 160 may generate the fundamental image and the harmonic image by performing processing such as compression, spatial filtering, temporal filtering, or DSC, on the fundamental components and the harmonic components.

A synthesization ratio of the fundamental components and the harmonic components is selected (313).

Selection of the synthesization ratio may be performed by the synthesization unit 150 or by a user's input. When the synthesization ratio is selected by the user's input, the fundamental image and the harmonic image may be displayed on the display unit 180 so that the user's selection may be assisted, as illustrated in FIG. 16 described above.

The synthesization ratio may be selected in the entire region or a partial region of the image or may be differently selected according to regions. For example, the synthesization ratio may be selected with respect to at least one of the lateral direction, the axial direction, and the elevational direction, for example.

The fundamental image and the harmonic image are synthesized according to the selected synthesization ratio (314).

The synthesization unit 150 may synthesize the fundamental image and the harmonic image according to the synthesization ratio selected by the user or the synthesization unit 150. For example, when a synthesization ratio of the fundamental image $I_F$ is selected as 100% and a synthesization ratio of the harmonic image $I_H$ is selected as 0%, the fundamental image $I_F$ is a synthesized image, and in an inverse case, the harmonic image $I_H$ is the synthesized image. Also, when the synthesization ratio of the fundamental image $I_F$ is selected as 40% and the synthesization ratio of the harmonic image $I_H$ is selected as 60%, the synthesized image may be generated by applying the synthesization ratio to each image.

The synthesized image may be displayed on the display unit 180, as illustrated in FIG. 16 or 17 described above, so that the result of synthesization may be informed to the user. The user may select a synthesization ratio again by watching a displayed result, and the synthesization unit 150 may synthesize two images according to a synthesization ratio that changes before the synthesization ratio is finalized and may display the synthesized image by using the display unit 180 in real time.

Figure 19:
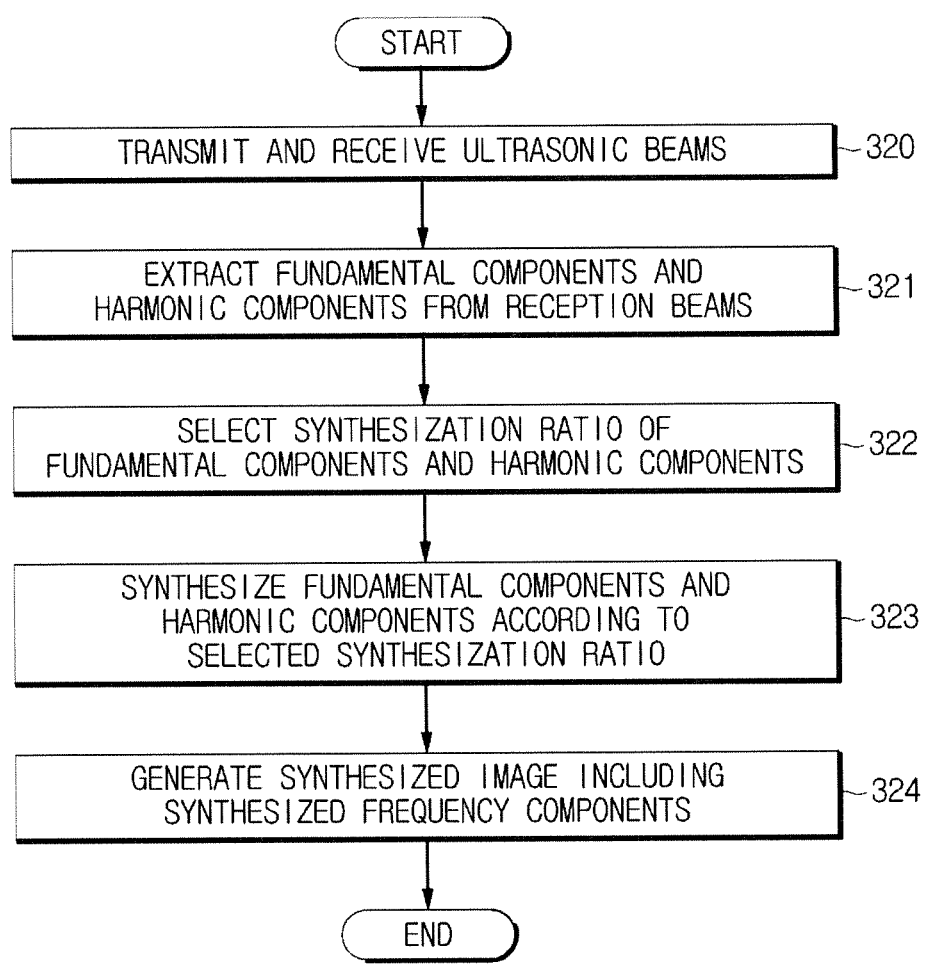
FIG. 19 is a flowchart of a method of controlling the ultrasonic diagnostic apparatus, in accordance with another embodiment of the present invention.

FIG. 19 is a flowchart of a method of controlling the ultrasonic diagnostic apparatus, in accordance with another embodiment of the present invention.

Referring to FIG. 19, in the present embodiment, transmission and reception of ultrasonic beams (320) and extraction of fundamental components and harmonic components from reception beams (321) are performed. These operations are as described in the embodiment of FIG. 18 and thus, a detailed description thereof will be omitted.

A synthesization ratio of the fundamental components and the harmonic components is selected (322), and the fundamental components and the harmonic components are synthesized according to a selected synthesization ratio (323).

Selection of the synthesization ratio of the fundamental components and the harmonic components may be performed by the synthesization unit 150, like in the above-described embodiment, or by the user. When the synthesization ratio of the fundamental components and the harmonic components is selected by the user, as illustrated in FIG. 16 described above, a fundamental image and a harmonic image may be displayed on the display unit 180 so that the user's selection may be assisted.

However, in the above-described embodiment, an object to be synthesized according to the selected synthesization ratio is the fundamental image and the harmonic image. However, in the present embodiment, the image is not synthesized but the fundamental components and the harmonic components are synthesized. That is, frequency components themselves are first synthesized.

Then, a synthesized image including the synthesized frequency components is generated (324).

The synthesized image may be displayed on the display unit 180. Like in the above-described embodiment, the user may check the displayed synthesized image and may select a synthesization ratio again or finalize the synthesization ratio.

In the above-described embodiments of FIGS. 18 and 19, transmission/reception of the ultrasonic beams is performed. However, extraction of the fundamental components and the harmonic components (311, 321) and generation of the synthesized image (314, 324) may be performed by using the reception beams that have been previously obtained and stored in the storing unit 190.

Alternatively, operations from generation of the fundamental image and the harmonic image (312) to generation of the synthesized image (314) may be performed by using the fundamental components and the harmonic components that have been previously extracted and stored in the storing unit 190, or operations from selection of the synthesization ratio (322) to generation of the synthesized image (324) may also be performed.

According to the ultrasonic diagnostic apparatus and the method of controlling the same described above, both the harmonic image and the fundamental image may be obtained by performing one scanning without changing an image mode or without performing new scanning, and the harmonic image and the fundamental image are synthesized so that the ultrasonic image having both advantages of two images may be provided to the user.

In addition, the harmonic image and the fundamental image are displayed and the user selects the synthesization ratio of the harmonic components and the fundamental components so that the synthesized image having the user's desired characteristics may be generated.

As described above, in accordance with embodiments of the present invention, an image caused by fundamental components of ultrasonic echo signals is generated and is synthesized with an image caused by harmonic components so that an image having both advantages of the images can be generated.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:
1. An ultrasonic diagnostic apparatus comprising:
a transmission beam generating unit that generates a plurality of sets of transmission beams by setting transmission beams which are transmitted in different transmission scan line positions and in which the sum of waveforms is 0, to one set;
a reception beam generating unit that generates reception beams with respect to at least one reception scan line in consideration of transmission delay of the transmission beams in each of the transmission scan lines;

a signal processing unit that extracts fundamental components and harmonic components from the reception beams, respectively;

an input unit to which selection of a synthesization ratio is input from a user;

a synthesization unit that generates synthesized signals by synthesizing the fundamental components and the harmonic components according to the synthesization ratio; and a display unit that displays a synthesized image comprising the synthesized signals, wherein the display unit visualizes the synthesization ratio quantitatively and displays the synthesized image according to the synthesization ratio as the synthesization ratio changes, in real time.

2. The ultrasonic diagnostic apparatus of claim 1, wherein the input unit receives the selection of the synthesization ratio in at least one of a lateral direction, an axial direction, and an elevational direction.

3. The ultrasonic diagnostic apparatus of claim 1, wherein the signal processing unit extracts the harmonic components by coupling the reception beams with respect to the same reception scan line.

4. The ultrasonic diagnostic apparatus of claim 1, wherein the signal processing unit extracts the fundamental components by subtracting at least two reception beams among the reception beams with respect to the same reception scan line.

5. The ultrasonic diagnostic apparatus of claim 1, wherein the signal processing unit performs filtering on noises included in the extracted fundamental components and harmonic components.

6. The ultrasonic diagnostic apparatus of claim 1, further comprising an image processing unit that generates a fundamental image comprising the fundamental components, a harmonic image comprising the harmonic components, and a synthesized image comprising the synthesized signals.

7. The ultrasonic diagnostic apparatus of claim 6, wherein the display unit further displays the fundamental image and the harmonic image.

8. The ultrasonic diagnostic apparatus of claim 1, further comprising a storing unit that stores the reception beams or the fundamental components and the harmonic components extracted from the reception beams.

9. An ultrasonic diagnostic apparatus comprising:
a transmission beam generating unit that generates a plurality of sets of transmission beams by setting transmission beams which are transmitted in different transmission scan line positions and in which the sum of waveforms is 0, to one set;

a reception beam generating unit that generates reception beams with respect to at least one reception scan line in consideration of transmission delay of the transmission beams in each of the transmission scan lines;

a signal processing unit that extracts fundamental components and harmonic components from the reception beams, respectively;

an image processing unit that generates a fundamental image comprising the fundamental components and a harmonic image comprising the harmonic components;

an input unit to which selection of a synthesization ratio is input from a user;

a synthesization unit that generates a synthesized image by synthesizing the fundamental image and the harmonic image according to the synthesization ratio; and a display unit that displays the synthesized image, wherein the display unit visualizes the synthesization ratio quantitatively and displays a synthesized image according to the synthesization ratio as the synthesization ratio changes, in real time.

10. The ultrasonic diagnostic apparatus of claim 9, wherein the input unit receives the selection of the synthesization ratio in at least one of a lateral direction, an axial direction, and an elevational direction.

11. The ultrasonic diagnostic apparatus of claim 9, wherein the display unit further displays the fundamental image and the harmonic image.

12. A method of controlling an ultrasonic diagnostic apparatus, the method comprising:
radiating a plurality of sets of transmission beams onto different transmission scan line positions by setting transmission beams in which the sum of waveforms is 0, to one set;

generating reception beams with respect to at least one reception scan line in consideration of transmission delay of the transmission beams in each of the transmission scan lines;

extracting fundamental components and harmonic components from the reception beams, respectively;

receiving selection of a synthesization ratio from a user;

generating synthesized signals by synthesizing the fundamental components and the harmonic components according to the synthesization ratio; and displaying a synthesized image comprising the synthesized signals, wherein the displaying of the synthesized image comprises visualizing the synthesization ratio quantitatively and displaying a synthesized image according to the synthesization ratio as the synthesization ratio changes, in real time.

13. The method of claim 12,
wherein the receiving the selection of the synthesization ratio comprises receiving selection of the synthesization ratio in at least one of a lateral direction, an axial direction, and an elevational direction.

14. The method of claim 12, wherein the extracting of the fundamental components and the harmonic components from the reception beams, respectively, comprises extracting the harmonic components by coupling the reception beams with respect to the same reception scan line.

15. The method of claim 12, wherein the extracting of the fundamental components and the harmonic components from the reception beams, respectively, comprises extracting the fundamental components by subtracting at least two reception beams among the reception beams with respect to the same reception scan line.

16. The method of claim 12, wherein the extracting of the fundamental components and the harmonic components from the reception beams, respectively, further comprises performing filtering on noises included in the extracted fundamental components and harmonic components.

17. The method of claim 12, further comprising generating a fundamental image comprising the fundamental components and a harmonic image comprising the harmonic components.

18. The method of claim 17, further comprising displaying the fundamental image and the harmonic image.

19. The method of claim 12, further comprising storing the reception beams or the fundamental components and the harmonic components extracted from the reception beams.

20. A method of controlling an ultrasonic diagnostic apparatus, the memthod comprising:

generating a plurality of sets of transmission beams in different transmission scan line positions by setting transmission beams in which the sum of waveforms is 0, to one set;

generating reception beams with respect to at least one reception scan line in consideration of transmission delay of the transmission beams in each of the transmission scan lines;

extracting fundamental components and harmonic components from the reception beams, respectively;

generating a fundamental image comprising the fundamental components and a harmonic image comprising the harmonic components;

receiving selection of a synthesization ratio from a user;

generating a synthesized image by synthesizing the fundamental image and the harmonic image according to the synthesization ratio; and displaying the synthesized image, wherein the displaying of the synthesized image comprises visualizing the synthesization ratio quantitatively and displaying a synthesized image according to the synthesization ratio as the synthesization ratio changes, in real time.

21. The method of claim 20,
wherein the receiving the selection of the synthesization ratio comprises receiving the selection of the synthesization ratio in at least one of a lateral direction, an axial direction, and an elevational direction.

22. The method of claim 20, further comprising displaying the fundamental image and the harmonic image.

* * * * *